United States Patent
Licari et al.

[11] Patent Number: 5,606,264
[45] Date of Patent: Feb. 25, 1997

[54] MOISTURE SENSOR FOR ELECTRONIC MODULES

[76] Inventors: James J. Licari, 15711 Arbela Dr., Whittier, Calif. 90803; Aram Tanielian, 7013 Cherty Dr., Rancho Palos Verdes, Calif. 92075

[21] Appl. No.: 426,044

[22] Filed: Apr. 21, 1995

[51] Int. Cl.$^6$ .................................................. H01C 13/00
[52] U.S. Cl. .......................... 324/763; 324/718; 324/719; 324/696; 422/82.03; 437/8
[58] Field of Search ............................. 422/82.03, 82.02; 437/8; 324/696, 694, 689, 718, 763, 719

[56] References Cited

U.S. PATENT DOCUMENTS

| | | | |
|---|---|---|---|
| 3,943,557 | 3/1976 | Frazee | 324/696 |
| 4,080,564 | 3/1978 | Nitta | 324/694 |
| 4,224,565 | 9/1980 | Sosniak | 324/694 |
| 4,272,986 | 6/1981 | Lowry | 324/696 |
| 4,775,831 | 10/1988 | Annamalai | 324/694 |

*Primary Examiner*—Maura K. Regan
*Assistant Examiner*—Jose M. Solis
*Attorney, Agent, or Firm*—Charles C. Logan, II

[57] ABSTRACT

Seepage of water and other impurities into hermetically sealed on plastic encapsulated modules leads to eventual device failure, as conductor material corrodes and opens, or electromigrates to establish conductive trails across a substrate, shorting the conductors. To forewarn of such failure, a sensing device defined as a separate chip is packaged in the same module with the circuit to be checked, with pinouts that can be tested with a circuit that is usually external. The sensor makes use of the moisture-induced migratory behavior that causes the problem, using a highly migratory metal or alloy to define paired electrodes spaced as closely as 2 micrometers apart. The metal of the electrodes undergoes rapid ionization and migration in the presence of trace amounts of moisture, dissolved ionic contaminants, and a small potential difference across the electrodes. Two volts applied to the sensor conductors by the sensor circuit will output a voltage if even a minute current is flowing between the electrodes permitting "go/no-go" decisions to be made regarding use of the module. The moisture which actuates the sensor, triggers the circuit long before the level of seepage and electromigratic represents present danger of circuit failure, and long before other types of sensors would indicate the existence of a problem.

16 Claims, 1 Drawing Sheet

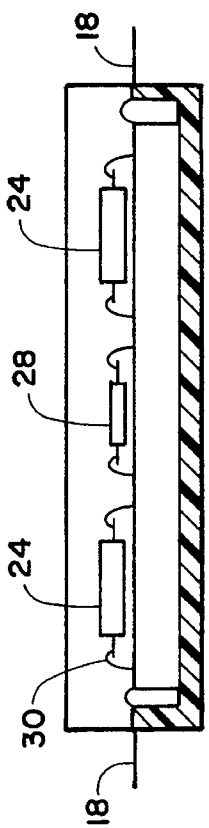
FIGURE 3
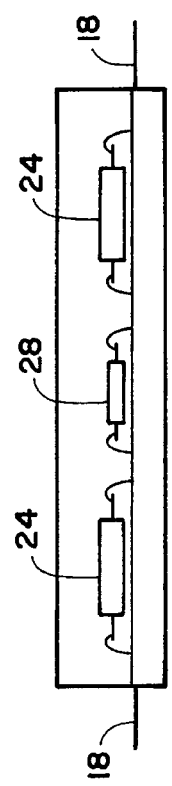
FIGURE 4
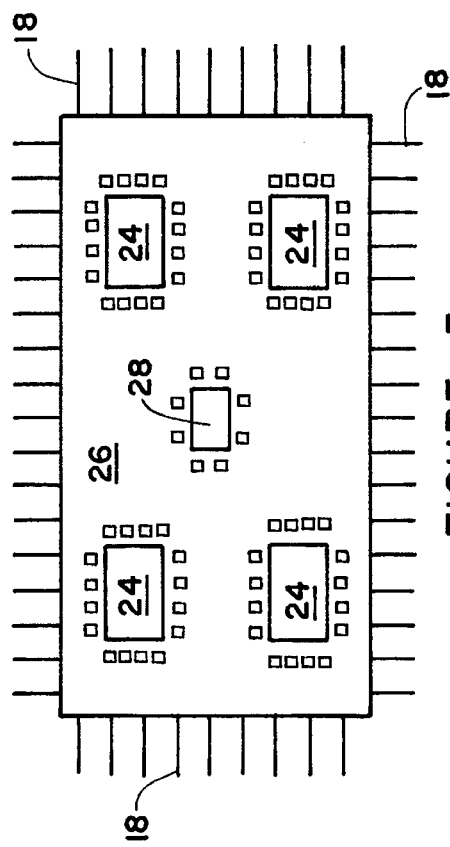
FIGURE 5
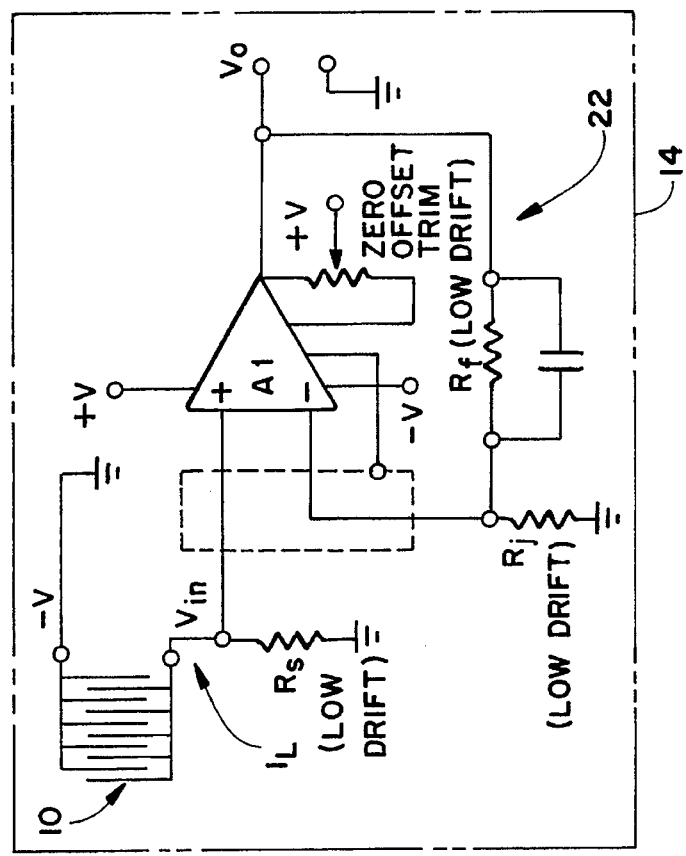
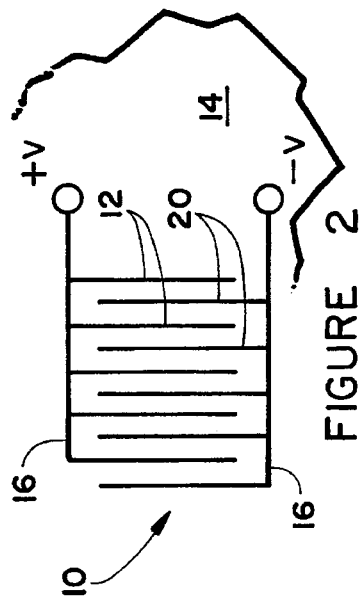
FIGURE 1
FIGURE 2

MOISTURE SENSOR FOR ELECTRONIC MODULES

BACKGROUND OF THE INVENTION

The invention relates to the failure of encapsulated circuits such as multi-chip modules resulting from contamination-induced physical deterioration of the conductor metal taking place within the package, generally after the device has been produced contaminant-free, but after being stored in a humid environment for a period of time. The most prevalent cause of such failure is the entry of moisture with dissolved ionic contaminants into the package.

The penetration of moisture into hermetically sealed electronic packages or the permeation of moisture through plastic in non-hermetically sealed packages, especially in the presence of small amounts of ionic contaminants (low parts per million of chloride ion, for example), is known to cause device or circuit failure. See for example, J. J. Licari, *Handbook of Polymer Coatings For Electronics*, (Noyes, 1990). The failure mechanisms are generally moisture and ion-induced chemical corrosion of a layer of thin film metallization, of aluminum, nichrome, or copper for example. These impurities cause electrochemical phenomena such as metal migration that catastrophically bridge and short out closely spaced conductors. Or, in bi-metallic wire bonds, such as gold to aluminum, resistances may increase and electrical opens occur while leakage currents increase. See G. Harman, *Wire Bond Reliability and Yield*, (ISHM Monograph, 1989), and J. J. Licari and L. Enlow, *Hybrid Microcircuit Technology Handbook*, (Noyes Publications, Park Ridge N.J., 1988).

It would be desirable to incorporate a moisture and contamination sensor in every multichip module so that the penetration of water through hermetically sealed or plastic-encapsulated electronic modules can be rapidly detected. Such a detector could be used to make "go-no go" decisions for modules that have been stored a long time in various harsh environments before deploying them in flight hardware and other critical applications, and would also be useful in deciding if modules already in service need to be replaced.

No such sensors exist today, despite considerable research and experimentation. Some tests destroy the modules, and most are awkward and time consuming to implement. To date, considerable work has been done on moisture sensors that are based on changes in the dielectric properties of thin film porous capacitor materials. This approach has been proven unsatisfactory because each chip had to be calibrated separately, and would then drift out of calibration after assembly and screen testing.

Currently used sensor chips such as Sandia Laboratory's ATC series are based on triple track resistors of thin film aluminum. However, they are not sensitive enough to show rapid resistance changes within or between the conductor lines, even after thousands of hours of biased 85/85 humidity/temperature exposure. Because of this, HAST (Highly Accelerated Stress Test) is being employed. However, it has been difficult to correlate HAST results with long term 85° C. /85% relative humidity test results. Cynthia Murphy et al of Microelectronics Computer Technology Corporation (MCC) reported at the 1994 Multichip Module Conference in Denver that the 141° C. temperature used by MCC in their HAST test was much too high for getting meaningful results on epoxy encapsulated chips. Degradation of the epoxy molecular structure occurred under HAST conditions which introduced new failure mechanisms and obfuscated any correlation with real-life expectancy. Although the Sandia chips are still excellent test sensors they are best used to initially qualify a material system or to obtain reliability data.

Special test chips have been designed to study moisture and ionic penetration onto active semiconductor devices based on changes in electrical resistance taking place due to corrosion occurring in thin film aluminum conductors (triple track resistors), or changes in capacitance that occur in porous oxide capacitors. (J. N. Sweet et al., *Proceedings of the 41st Electronic Components and Technology Conference*, 1991).

Other approaches depend on capacitance changes occurring in a capacitor device or a porous dielectric due to the condensation of moisture. These techniques require cooling a hermetically sealed package until the dew point of the internal ambient fluid is reached and the moisture condenses. U.S. Pat. No 4,224,656 to Sosniak and 4588943 to Hirth speak to this. Again these approaches require careful calibration of each chip, which is expensive to start with, and exposure to elevated temperatures throws off the settings and re-calibration is required. Still other approaches measure leakage currents or conductance of an integrated circuit, which has moisture condensing between the conductor lines resulting in a measurable increase in conductance due to the presence of the electrolyte.

Whatever the mechanism, it is particularly important to have some kind of moisture reporting device for electronics modules such as aircraft, missile or computer components, that have been stored for extended periods of time in warm, humid environments. Beyond military and high-tech applications and anything involving electronics, a suitable moisture sensor/indicator could also be used in any moisture-sensitive applications such as packaged commercial or consumer optical instruments, foods or pharmaceuticals.

There is a need for such a simple chip-mounted moisture sensing device that can serve a "go/no go" function, incorporated in multichip circuits to determine if moisture has penetrated and has affected, or has a high likelihood of affecting, the reliability of the modules, and which may be broader in its application to be useful in many situations in which the presence of moisture is of concern.

SUMMARY OF THE INVENTION

Silver conductor migration is a failure mechanism that has caused millions of dollars in damage, and now will be exploited and used beneficially to mitigate the damage it has caused. Silver migration between two slightly biased terminals occurs in a matter of minutes if moisture or water and some ionic residues are present. Silver dissolves as cations at the anode, the ions are attracted to the cathode whereupon they are reduced by capturing an electron and then migrate (deposit and grow) as metallic silver, ultimately bridging the gap and shorting the circuit. The mechanism for silver migration and dendritic growth has been described in the literature Catastrophic failures occur if sufficient moisture and ions are present. If not, measurable leakage current will still flow when even minute quantities of moisture an d ions present occur that can be measured. If silver migration occurs on these chips, even if the circuit devices are still functional, the circuit should be considered in jeopardy since the migration is proof that the moisture has penetrated to the active devices and to the interconnect surface.

The invention makes beneficial use of metal migration by using closely spaced conductor lines consisting of silver, indium or other migratory metal or metal alloy applied to a substrate. In the presence of moisture and certain ionic contaminants such as chloride, and a DC potential difference of as little as 2 volts, the resistance between the conductors will noticeably decline and will be reported by the sensor's circuit.

Under these conditions of contamination, electromigration occurs rapidly and the drop in resistance is apparent in a matter of minutes, as metal is freed from the conductors by electrolysis and migrates across the substrate to form a conductive trail. Even if the rest of the circuit is functioning perfectly despite the moisture, providing no other clue to its impending malfunction, the sensor will alert technicians to the presence of moisture and contaminants. The phenomenon of silver migration takes place so rapidly when these conditions exist that leakage can be reported in real time to warn that the module is at risk for eventual failure long before failure is imminent.

BRIEF DESCRIPTION OF THE DRAWINGS

FIG. 1 is a schematic diagram of the circuit used in the invention, including the sensor;

FIG. 2 is a diagrammatic illustration of one form that the sensor element of the invention may take;

FIG. 3 is a diagrammatic view of a hermetically sealed package;

FIG. 4 is a diagrammatic view of a polymer coated encapsulated microcircuit; and, FIG. 5 is a diagrammatic top plan view of the layout of the sensor chip on an interconnect substrate of the circuit to be monitored, in a multichip module of the type shown in FIGS. 3 and 4.

DETAILED DESCRIPTION OF THE PREFERRED EMBODIMENTS

The sensor element 10 of the device consists of closely spaced, preferably interdigitated silver conductor lines such as those shown in FIG. 2 at 12. The sensor element is patterned on substrate 14. The individual conductor combs 16 of the sensor element may be fabricated on silicon or some other material such as polyamide coated alumina or silicon substrate, which is commonly found in thin film multilayer, multichip modules. Conductor lines 12 and interline spacing 20 may be as small as two micrometers or as great as several mils. The comb configuration of FIG. 2 is one example of many different arbitrarily selectable layout designs, reliability and sensitivity being correlated with the length of the interface and conductor spacing.

The silver may be deposited on the substrate by any one of a number of well known thin film vapor evaporation or sputtering processes. For a review and explanation of these see R. Bunshah, *"Deposition Technologies For Films And Coatings* (Noyes Publications, Park Ridge, N.J., 1994). Thick film screen printing processes, or combinations of thick and thin film techniques can be used as well. If deposited by thin film, the silver film is subsequently photolithographically etched to form the interdigitated pattern. If created as a thick film, the sensor can be formed by screenprinting and firing a thick-film paste consisting conductive migratory metallic material, such as of silver, indium or an alloy.

There are three electronic items involved: 1) the sensor element itself, consisting of the two conductive combs 16 or their equivalents defined on a substrate 14; 2) the sensor circuit 22 of FIG. 1 designed for testing the sensor element; and, 3) the object circuit, the circuit that will be monitored or tested, illustrated in FIGS. 3–5. In the principal configuration the sensor element is defined as a separate chip packaged in the module with the circuit to be tested. The sensor test circuit is separate and is typically used one time only on a module. It is connected to the sensor element pinouts 18, and applies a low voltage across the electrodes for a short time, testing for conductivity. If ion contaminated moisture has seeped into the package, the migration of silver will begin instantly, and within a few minutes the dendritic paths between conductors will enable a current that is measurable, and the circuit will have failed the test. Less than ten minutes is generally required, but the test should be run for 20 minutes to be sure the module is good. There is nothing else available that can accomplish this result in real time and non-invasively, without destroying the module.

Other arrangements of the three components are possible, dictated by considerations of function and convenience. The test circuit could be integrated with the sensor element on the same chip, or on a separate chip but in the same package. If the circuit were designed to periodically test the object circuit automatically and trigger an alarm if appropriate, or be available for periodic or erratic polling by an operator, one of these arrangements, in which both the test circuit and the sensor element are contained within the envelope of the module, would be a logical choice In the event that a single IC were the object circuit, the test circuit and sensor element could be defined right on the IC substrates along with the object circuit. This configuration is not currently planned for production, but is a logical extension of the concept. For now, manufacturing will be directed toward multi-chip modules.

The device may be fabricated in a thin or thick film hybrid microcircuit or a multichip module. It may be packaged in hermetically sealed ceramic, metal, or ceramic-metal cavity packages as shown in FIG. 3, or molded in plastic glob-topped circuit packages shown in FIG. 4. In these figures and FIG. 5, an example is shown of an object circuit including four IC's 24 mounted on an interconnect substrate 26 and encapsulated with the central sensor chip 28 which is connected by lead wires 30 to the interconnect substrate. This chip could be either the bare sensor or the sensor and its test circuit. The hermetically sealed package of FIG. 3 is encased in a box of alumina, aluminum nitride, Kovar® or some other metal, whereas the FIG. 4 package is encapsulated in polymeric plastic or the equivalent. These are two examples of the many different types of packages used for circuits, any one of which would be appropriate for incorporation of the sensor chip or the sensor chip with the test circuit in the envelope with the object circuit.

The circuit used to test the sensor element conductivity is shown in FIG. 1. A controlled voltage is applied to the sensor conductors, and in the case of a one-shot test as opposed to periodic or constant monitoring, the voltage level does not need to be controlled or known with any significant accuracy since the module either passes the test, or it does not. The sensor is very sensitive to resistance changes, but it does not need to be accurate. However, it must be applied to the circuit long enough for silver or metal migration to occur in the presence of ion-laden moisture, which should take no more than 20 minutes. Leakage current, if any, flows between the interleaved conductor groups on application of a voltage across resistor $R_s$ As indicated on the FIG. 1 schematic, the values and their mathematical interactions are as follows:

$$V_o = I_L R_S \left( \frac{R_F}{R_I} \right) + 1$$

if $R_s = 100K\Omega$ then $\Delta V_{IN} = 100 \frac{\mu V}{\eta A}$ if $\left( \frac{R_F}{R_I} \right) + 1 = 100$ Then $\Delta V_o = 10$ mV/$\eta A$ Operational amplifier A1 is an ultra-low bias, low drift type such as Burr Brown's OPA 104 which has an input bias current less than 0.075 picoamps and a drift of less than 10 uV/°C. Its input impedance is $10^{15}$ Ohms. Leakage sensor resistor ($R_s$) and gain set resistor ($R_J$) are matched for drift tracking. These values provide a sensor which has an output voltage proportional to the current in the leakage sensor with a $\Delta V_o/I_o$ of 10 mV per nanoamp leakage. Output impedance is about 8 K-Ohm and can be used to drive a recorder directly.

The output may be periodically sampled, or connected to a signal device such as an LED to automatically alert the technician of an error condition. More commonly the leads would remain open except for the relatively brief duration of the test when the part is ready for installation. A minute nanoamp leakage current produces a measurable 10 millivolt output, and any measurable leakage (current leakage) is reason enough to scrap the pan, or at least avoid using it in a critical capacity.

This is the capability that has heretofore been unavailable. That is the capability of checking the module without destroying it, in a reasonable time (20 minutes or less) with a definitive result on which to base a go/no go decision with regard to the installation of the module, and if the indication is "go", the decision can be made with a high degree of confidence that the tested module is not leaking at all, and at least at this point in time is not headed for failure.

We claim:

1. A moisture and contamination sensor for reporting the presence of moisture-borne contaminants, comprising:

(a) a sensor element defining a pair of spaced conductors mounted on an insulative substrate and being made of a migratory metal that migrates in the presence of a small electrical potential and minute amounts of ionic contaminant-laden moisture, said migratory metal having a first ionization potential of less than 8.0 electron volts and having a hydroxide form which has a dissociation constant of at least $10^{-10}$; and, (b) connect means connected to said conductors and being connectible to a test circuit capable of applying a small electrical bias potential across said conductors for a period of time, to cause dendritic bridging of said conductors on said substrate in less than an hour if moisture is present, and then a test voltage, whereby observance of a current induced by said test voltage would indicate the presence of moisture-borne contaminants on said sensor element.

2. A sensor according to claim 1 wherein said sensor element is predominantly silver.

3. A sensor according to claim 2 wherein said conductors each define spaced parallel fingers and the respective fingers are interdigitated in opposition to increase the effective exposed length of the opposed conductors to encourage dendritic connection formation between said conductors in the presence of moisture and said small electrical potential.

4. A sensor according to claim 3 wherein said conductors are spaced apart on the average between two micrometers and 50 micrometers.

5. A sensor according to claim 3 wherein said spaced conductors are defined as film on said substrate.

6. A sensor according to claim 5 wherein said sensor element is defined as a separate chip mountable on an interconnect substrate.

7. A sensor according to claim 5 wherein said interconnect substrate is a substrate of a circuit to be monitored and said sensor element shares said interconnect substrate with said circuit to be monitored.

8. A sensor according to claim 5 wherein said sensor element is a thin film that is photolithographically formed on said substrate.

9. A sensor according to claim 5 wherein said sensor is formed by screen printing and firing a thick-film predominantly silver paste.

10. A sensor according to claim 1 and wherein said test circuit is a sensor amplifier test circuit, and said sensor includes said sensor amplifier test circuit, and same outputs a voltage which is a function of the current between said conductors established by dendritic growth occurring on said substrate between the conductors caused by application of a bias voltage.

11. A sensor according to claim 10 wherein both said sensor element and said sensor circuit are defined as respectively separate chips.

12. A sensor according to claim 3 wherein said sensor circuit and said sensor element are both mounted within the envelope of the same multichip module.

13. A sensor according to claim 10 wherein said circuit and sensor element are integrally formed in the same chip and said chip is mountable in a multichip module.

14. A sensor according to claim 10 wherein said circuit and sensor element are integrally formed on the substrates of the same chip in which a circuit to be monitored resides such that a single integrated circuit chip is defined by said sensor element, said test circuit and the circuit to be monitored.

15. A method of determining whether or not moisture has breached the seal of a sealed compartment comprising the following steps:

(a) disposing a pair of spaced electrodes, composed primarily of silver, on a substrate within said compartment during manufacture of same;

(b) applying a bias voltage of between two and fifteen volts across said conductor pair for a period of time to enable dendritic growth to substantially bridge between the conductors if there is contaminant-laden moisture in the compartment;

(c) after said period of time has passed, applying a test voltage across said electrodes, determining whether current flows therebetween at a measurable level, and if so declaring said sealed compartment to have been breached.

16. A method according to claim 15 wherein said period of time is no greater than an hour, subsequent to which dendritic growth either has or has not occurred.

\* \* \* \* \*